(12) United States Patent
Horng et al.

(10) Patent No.: US 8,754,772 B2
(45) Date of Patent: Jun. 17, 2014

(54) NON-CONTACT VITAL SIGN SENSING SYSTEM AND SENSING METHOD USING THE SAME

(75) Inventors: Tzyy-Sheng Horng, Kaohsiung (TW); Fu-Kang Wang, Kaohsiung (TW); Kang-Chun Peng, Kaohsiung (TW)

(73) Assignees: Industrial Technology Research Institute, Hsinchu (TW); National Sun Yat-Sen University, Kaohsiung (TW)

( * ) Notice: Subject to any disclaimer, the term of this patent is extended or adjusted under 35 U.S.C. 154(b) by 56 days.

(21) Appl. No.: 13/456,849

(22) Filed: Apr. 26, 2012

(65) Prior Publication Data

US 2012/0209087 A1 Aug. 16, 2012

Related U.S. Application Data

(63) Continuation-in-part of application No. 12/886,522, filed on Sep. 20, 2010.

(30) Foreign Application Priority Data

Oct. 12, 2011 (TW) .............................. 100136990 A

(51) Int. Cl.
*G08B 23/00* (2006.01)
(52) U.S. Cl.
USPC ....................... 340/573.1; 340/539.1; 340/604
(58) Field of Classification Search
USPC ............ 340/573.1, 604, 539.12, 539.13, 540, 340/539.1, 539.11; 600/301, 485, 534
See application file for complete search history.

(56) References Cited

U.S. PATENT DOCUMENTS

| | | | |
|---|---|---|---|
| 3,221,260 A | 11/1965 | Henrion | |
| 3,479,607 A | 11/1969 | Ruthroff | |
| 4,517,982 A | 5/1985 | Shiga et al. | |
| 4,600,890 A | 7/1986 | Horvat | |
| 4,646,754 A | 3/1987 | Seale | |
| 4,953,010 A | 8/1990 | Cowley | |
| 4,958,638 A | 9/1990 | Sharpe et al. | |
| 4,991,585 A | 2/1991 | Mawhinney | |
| 5,458,124 A * | 10/1995 | Stanko et al. ................. | 600/509 |

(Continued)

FOREIGN PATENT DOCUMENTS

| | | |
|---|---|---|
| CN | 101006915 | 8/2007 |
| CN | 101093995 | 12/2007 |

(Continued)

OTHER PUBLICATIONS

English language translation of abstract of CN 101006915 (published Aug. 1, 2007).

(Continued)

*Primary Examiner* — Daniel Previl
(74) *Attorney, Agent, or Firm* — McClure, Qualey & Rodack, LLP

(57) ABSTRACT

A non-contact vital sign sensing system including a vital sign sensing module and at least one body movement interference cancellation module is provided. The vital sign sensing module and the at least one body movement interference cancellation module are under a self-injection locking (SIL) mode. The vital sign sensing module senses an isotropic vital sign of a body. A mutual injection locking (MIL) mode is achieved between the vital sign sensing module and the at least one body movement interference cancellation module to sense the anisotropic body movement signal and to cancel the body movement interference.

16 Claims, 13 Drawing Sheets

(56) References Cited

U.S. PATENT DOCUMENTS

| | | | |
|---|---|---|---|
| 5,650,749 | A | 7/1997 | Main |
| 6,133,802 | A | 10/2000 | Ma |
| 6,369,647 | B1 | 4/2002 | Main et al. |
| 6,369,659 | B1* | 4/2002 | Delzer et al. ............. 331/10 |
| 7,103,132 | B1 | 9/2006 | Baba |
| 7,740,588 | B1 | 6/2010 | Sciarra |
| 8,147,409 | B2 | 4/2012 | Shifrin |
| 2006/0040739 | A1* | 2/2006 | Wells ..................... 463/37 |
| 2007/0241864 | A1 | 10/2007 | Nagai |
| 2008/0079636 | A1 | 4/2008 | Mohamadi |
| 2008/0146944 | A1 | 6/2008 | Tao et al. |
| 2008/0183053 | A1* | 7/2008 | Borgos et al. ............ 600/301 |
| 2009/0278728 | A1 | 11/2009 | Morgan et al. |
| 2010/0152600 | A1 | 6/2010 | Droitcour et al. |
| 2010/0198083 | A1* | 8/2010 | Lin et al. ................ 600/484 |
| 2010/0249630 | A1 | 9/2010 | Droitcour et al. |

FOREIGN PATENT DOCUMENTS

| | | |
|---|---|---|
| EP | 2180593 A1 | 4/2010 |
| TW | 200901940 A | 1/2009 |
| TW | 201120790 | 6/2011 |
| TW | I347108 | 8/2011 |

OTHER PUBLICATIONS

English language translation of abstract of CN 101093995 (published Dec. 26, 2007).

English language translation of abstract of TW 201120790 (published Jun. 16, 2011).

English language translation of abstract of TW I347108 (published Aug. 11, 2011).

Fletcher, R., et al.; "Low-Cost Differential Front-End for Doppler Radar Vital Sign Monitoring;" IEEE; 2009; pp. 1325-1328.

Main, E., et al.; "FM Demodulation Using an Injection-Locked Oscillator;" IEEE; 2000; pp. 135-138.

Biswas, B.N., et al.; "A Doubly Tracking Discriminator;" IEEE; 2009; pp. 1-4.

Tarar, M., et al.; "Injection-Locked Phase-Locked Loop for BPSK Coherent Demodulation: Theory and Design;" IEEE 2007; pp. 387-390.

Chattopadhyay, T., et al.; "A New Microwave Discriminator;" IEEE; 2003; pp. 1078-1081.

Chattopadhyay, T.P., et al.; "Improved X-Band FM Discriminator;" IEEE Transactions on Microwave Theory and Techniques; vol. MTT-34; No. 4; Apr. 1986; pp. 442-446.

Non-Final Office Action for U.S. Appl. No. 13/484,732 issued by the USPTO on Jun. 6, 2013.

Droitcour, et al.: "Range Correlation and I-Q Performance Benefits in Single-Chip Silicon Doppler Radars for Noncontact Cardiopulmonary Monitoring"; IEEE Transactions on Microwave Theory and Techniques, vol. 52, No. 3, Mar. 2004; pp. 838-848.

Xiao, et al.: "Frequency-Tuning Technique for Remote Detection of Heartbeat and Respiration Using Low-Power Double-Sideband Transmission in the Ka-Band"; IEEE Transactions on Microwave Theory and Techniques, vol. 54, No. 5, May 2006; pp. 2023-2032.

Mostafanezhad, et al.: "Application of Empirical Mode Decomposition in Removing Fidgeting Interference in Doppler Radar Life Signs Monitoring Devices"; 31st Annual International Conference of the IEEE EMBS Minneapolis, Minnesota, USA, Sep. 2-6, 2009; pp. 340-343.

Yan, et al.: "Effects of I/Q Mismatch on Measurement of Periodic Movement Using a Doppler Radar Sensor"; 1Department of Electrical and Computer Engineering, University of Florida; 978-1-4244-4726-8/10/$25.00 © 2010 IEEE; pp. 196-199.

TW Office Action dated Dec. 16, 2013.

* cited by examiner

NON-CONTACT VITAL SIGN SENSING SYSTEM AND SENSING METHOD USING THE SAME

This is a continuation-in-part application of U.S. application Ser. No. 12/886,522, filed Sep. 20, 2010, which claims the benefit of Taiwan application Serial No. 099115691, filed May 17, 2010. The present application also claims the benefit of Taiwan application Serial No. 100136990, filed Oct. 12, 2011 These disclosures are incorporated by reference herein in their entireties.

TECHNICAL FIELD

The disclosure relates in general to a non-contact vital sign sensing system and a sensing method using the same, and more particularly to a non-contact vital sign sensing system which cancels body movement interference and a sensing method using the same.

BACKGROUND

As living standards continue to improve, people are becoming increasingly concerned with their health. Since many people may neglect their body warning messages, a number of vital sign measuring devices are provided for monitoring the vital signs of people so that people are aware of their health.

Currently, there are two types of vital sign sensing apparatuses, namely, contact type and non-contact type. The contact vital sign sensing apparatus performs measurement by touching people's body and has simple circuit constitution. However, people may feel uncomfortable if the contact vital sign sensing apparatus contacts his/her skin for a long time.

In comparison to the contact vital sign sensing system, the non-contact vital sign sensing system reduces people's uneasiness during sensing. Meanwhile, the non-contact vital sign sensing system is free of space restriction and used in remote medical care or vital signal monitoring.

Therefore, the disclosure provides a non-contact vital sign sensing system and method which cancel body movement interference during sensing.

SUMMARY

The disclosure is directed to a non-contact vital sign sensing system and method which sense a vital sign according to a self-injection locking (SIL) and cancel body movement interference according to a mutual injection locking (MIL).

According to an exemplary embodiment of the present disclosure, a non-contact vital sign sensing system including a vital sign sensing module and at least one body movement interference cancellation module is provided. The vital sign sensing module for sensing a vital sign of an object includes a first antenna, a first voltage control oscillator (VCO), a frequency demodulation unit, and a signal processing unit. The first antenna transmits a first transmission wireless signal to the object and receives a first reflected wireless signal reflected by the object. The first VCO is directly connected to the first antenna for outputting the first transmission wireless signal to the first antenna and receiving the first reflected wireless signal via the first antenna, such that the vital sign sensing module is under a self-injection locking (SIL) mode. The frequency demodulation unit is coupled to the first VCO for demodulating a frequency variation of the first VCO. The signal processing unit is coupled to the frequency demodulation unit and the first VCO for obtaining the vital sign of the object from the frequency variation of the first VCO and for determining a first oscillation frequency of the first VCO. Each body movement interference cancellation module is wirelessly coupled to the vital sign sensing module for canceling a body movement signal of the body. Each body movement interference cancellation module includes a second antenna and a second VCO. The second antenna transmits a second transmission wireless signal to the object and receives a second reflected wireless signal reflected by the object. The second VCO is directly connected to the second antenna for outputting the second transmission wireless signal to the second antenna and for receiving the second reflected wireless signal via the second antenna, such that the at least one body movement interference cancellation module is under an SIL mode. The first antenna transmits the first transmission wireless signal to the second antenna of the at least one body movement interference cancellation module. The first transmission wireless signal is received by the second VCO via the second antenna. The second antenna transmits the second transmission wireless signal to the first antenna of the vital sign sensing module, and the second transmission wireless signal is received by the first VCO via the first antenna, such that a mutual injection locking (MIL) mode is achieved between the vital sign sensing module and the at least one body movement interference cancellation module.

According to another exemplary embodiment of the present disclosure, a non-contact vital sign sensing method includes: a vital sign sensing module transmitting a first transmission wireless signal to an object and receiving a first reflected wireless signal reflected by the object so that a first VCO is under a self-injection locking (SIL) mode; a body movement interference cancellation module for canceling a body movement signal of the object, transmitting a second transmission wireless signal to the object and receiving a second reflected wireless signal reflected by the object such that a second VCO is under the SIL mode; and the first transmission wireless signal is received by the vital sign sensing module, and the second transmission wireless signal is received by the body movement interference cancellation module so that a mutual injection locking (MIL) is achieved between the first VCO and the second VCO.

It is to be understood that both the foregoing general description and the following detailed description are exemplary and explanatory only and are not restrictive of the disclosed embodiments, as claimed.

Figure 1A:
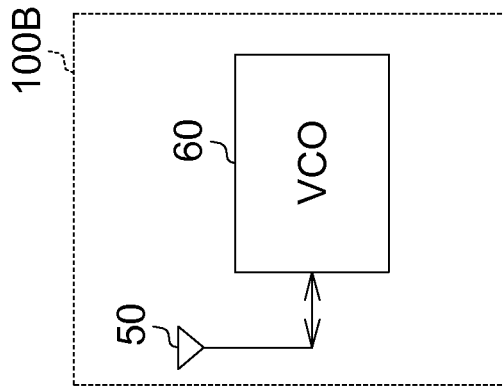
FIGS. 1A and 1B show system block diagrams of a non-contact vital sign sensing system according to exemplary embodiments of the disclosure.
Figure 1A:
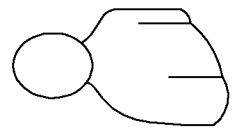
Figure 1A:
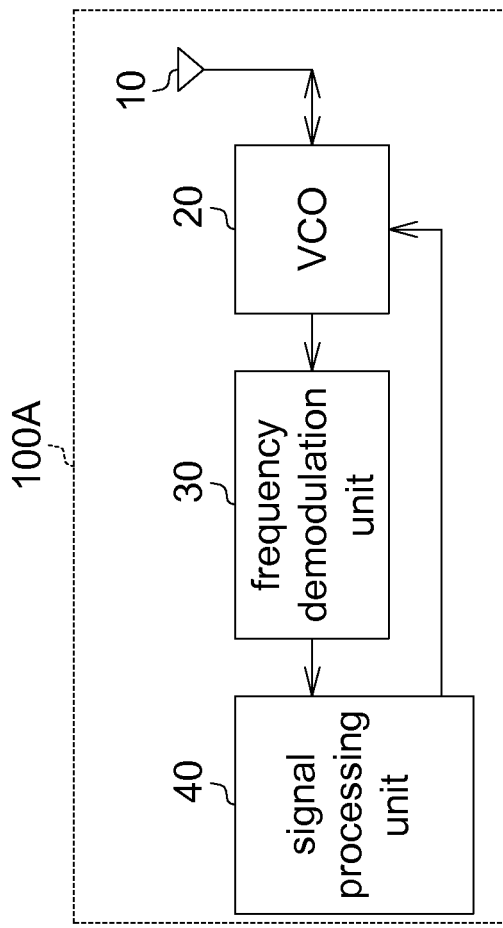

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

DETAILED DESCRIPTION OF THE DISCLOSURE

A non-contact vital sign sensing system is disclosed below in embodiments of the disclosure. Operations of the non-contact vital sign sensing system are based on the Doppler Effect which is generated when a wireless electrical wave is interfered by an object vital sign (such as breathing and heartbeat) such that the frequency variation of the wireless electrical wave signal corresponds to the vital sign.

In embodiments of the disclosure, the voltage control oscillator (VCO) tracks the electrical wave signal generating the Doppler effect to sense the vital sign of a body by a self-injection locking (SIL) of the respective VCOs and cancels body movement interference (regular body movement or random body movement) during sensing by a mutual injection locking (MIL) between the VCOs. During sensing, the object body movement generates additional Doppler shift and if the body movement information is not cancelled, then the sensing accuracy will decrease in principle.

In embodiments of the disclosure, the frequency variation of a body vital sign is demodulated into a voltage signal by a frequency demodulator, and the voltage signal is processed by a signal processing unit into vital signs such as breathing and heartbeat.

In embodiments of the disclosure, the non-contact vital sign sensing system includes a vital sign sensing module and one or more body movement interference cancellation modules. If the vital sign sensing module and the body movement interference cancellation module(s) are under an SIL mode, an isotropic vital sign and an anisotropic body movement signal may be obtained. Accordingly, there are a plurality of transmission wireless signals.

Figure 1B:
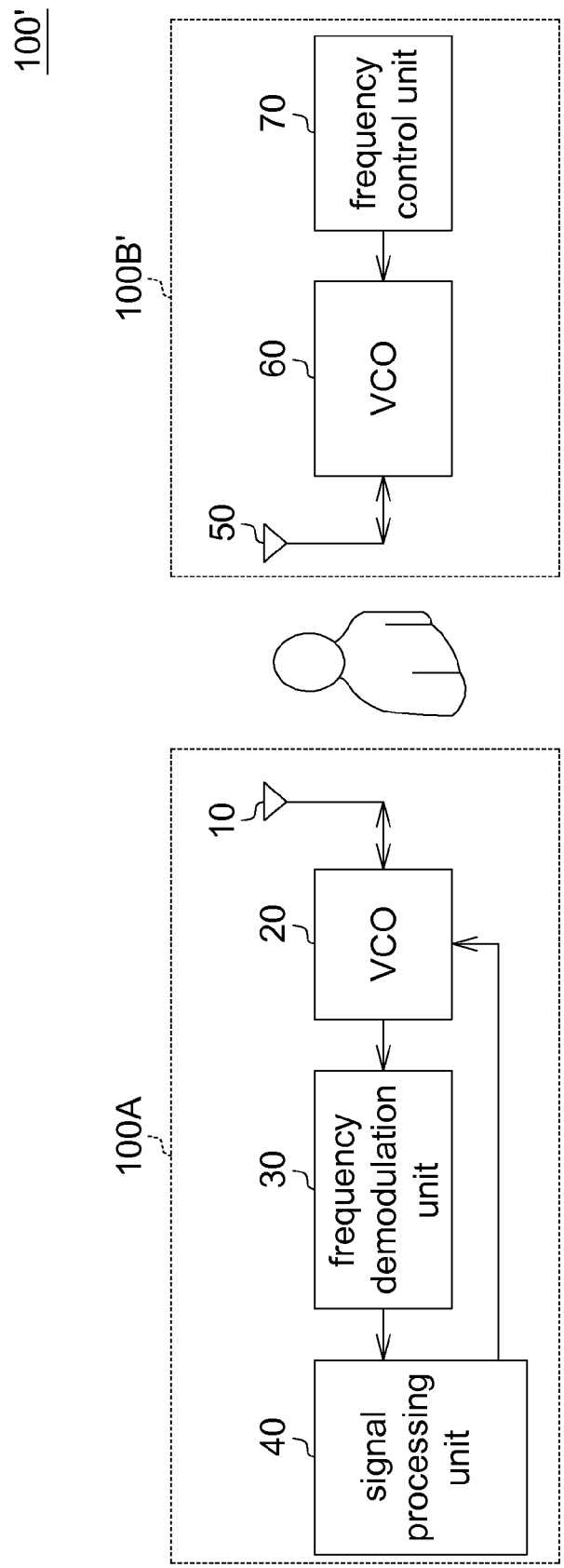

Referring to FIGS. 1A and 1B, system block diagrams of a non-contact vital sign sensing system 100 and 100' according to exemplary embodiments of the disclosure is shown. The non-contact vital sign sensing system 100 includes a vital sign sensing module 100A and a body movement interference cancellation module 100B. The vital sign sensing module 100A includes an antenna 10, a VCO 20, a frequency demodulation unit 30 and a signal processing unit 40. The body movement interference cancellation module 100B includes an antenna 50, a VCO 60. The body movement interference cancellation module 100B' of the non-contact vital sign sensing system 100' includes a frequency control unit 70.

The antenna 10 is electrically connected to an output port of the VCO 20 for transmitting an output signal of VCO 20 towards the object (such as to the heart at the front side of the object body). The reflected signal is received by the antenna 10 and the vital sign sensing module 100A is operated under an SIL mode. Due to the Doppler Effect, the frequency of the signal transmitted to the object from the antenna 10 is different from the frequency of the signal reflected from the object.

The oscillation frequency of the VCO 20 of the vital sign sensing module 100A is determined by the signal processing unit 40. Since the VCO 20 outputs and receives signals via the same antenna 10, the VCO 20 is under an SIL mode. That is, the output signal of the VCO 20 is transmitted via the antenna 10, and the signal received by the antenna 10 is inputted to the VCO 20, such that the VCO 20 is under an SIL mode. In the present disclosure, "the VCO 20 is under an SIL mode" is almost the same as "the vital sign sensing module 100A is under an SIL mode".

The output port of the VCO 20 of the vital sign sensing module 100A is electrically connected to an input port of the frequency demodulation unit 30. The frequency demodulation unit 30 demodulates the frequency variation of the VCO 20 into a voltage signal. The output port of the frequency demodulation unit 30 is electrically connected to an input port of the signal processing unit 40. The demodulated signal is processed by the signal processing unit 40 (such as but not limited to digital filtering and/or Fourier transform) for obtaining wave patterns and frequency patterns of breathing and heartbeat in time domain.

The output port of the signal processing unit 40 is electrically connected to a voltage input port of the VCO 20 for determining the oscillation frequency of the VCO 20.

The antenna 50 is electrically connected to an output port of the VCO 60 for transmitting an output signal of the VCO 60 towards the object (such as to the heart at the back side of the body). After the reflected signal is received by the antenna 50, the body movement interference cancellation module 100B/100B' is operated under an SIL mode. Due to the Doppler Effect, the frequency of the signal transmitted to the object from the antenna 50 is different from the frequency of the signal reflected from the object.

The oscillation frequency of the VCO 60 of the body movement interference cancellation module 100B' is determined for example by the frequency control unit 70. The VCO 60 outputs and receives signals via the same antenna 10 and the VCO 20 is under the SIL mode. That is, the output signal of the VCO 60 is transmitted via the antenna 50, and the signal received by the antenna 50 is inputted to the VCO 60, such that the VCO 60 is under the SIL mode. In the present disclosure, "the VCO 60 is under an SIL mode" is almost the same as "the body movement interference cancellation module 100B/100B' is under an SIL mode".

The output signal of the VCO 20 is transmitted to the antenna 50 via the antenna 10 and received by the VCO 60. Likewise, the output signal of VCO 60 is transmitted to the antenna 10 via the antenna 50 and received by the VCO 20. Such that an MIL mode is achieved between the VCO 20 and the VCO 60. In the present disclosure, "an MIL mode is achieved between the VCO 20 and the VCO 60" is almost the same as "an MIL mode is achieved between the vital sign sensing module 100A and the body movement interference cancellation module 100B/100B'."

In the body movement interference cancellation module 100B', the output port of the frequency control unit 70 is electrically connected to an input port of the VCO 60 for determining the oscillation frequency of the VCO 60. In the present embodiment of the disclosure, the oscillation frequency of the VCO 20 is almost the same with that of the VCO 60.

In the present embodiment of the disclosure, the signal transmitted by the vital sign sensing module 100A is received by the body movement interference cancellation module 100B/100B' and vice versa, so as to achieve MIL. Since breathing and heartbeat respectively make the lung and the heart expand and contract periodically during sensing, the vital sign is an isotropic signal to the vital sign sensing module 100A and the body movement interference cancellation module 100B/100B'. Since the body movement is in one direction, the body movement signal is an anisotropic signal to the vital sign sensing module 100A and the body movement interference cancellation module 100B/100B'.

For example, when the heart expands, both the vital sign sensing module 100A and the body movement interference cancellation module 100B/100B' sense that the heart gets closer, and this is the meaning of "the vital sign is an isotropic signal". If the body moves towards the vital sign sensing module 100A, the vital sign sensing module 100A senses that the body approaches, but the body movement interference cancellation module 100B/100B' senses that the body moves away, and this is the meaning of "the body movement signal is an anisotropic signal". In the present embodiment of the disclosure, the interference by the body movement is cancelled via the MIL between the sensing modules 100A and 100B/100B'. The body movement signal is anisotropic to the sensing modules 100A and 100B/100B' and thus is cancelled by the sensing modules 100A and 100B/100B'. That is, if the sensing module 100A and 100B/100B' are placed in such a manner that the body movement signal is isotropic to the sensing modules 100A and 100B/100B', then the body movement signal may not be cancelled by the sensing modules 100A and 100B/100B'.

During sensing, if the body moves, then physiological information (such as breathing and heartbeat) and body movement signal are sensed at the position of the chest cavity, but only the body movement signal is sensed at the position of the abdominal cavity.

Figure 2:
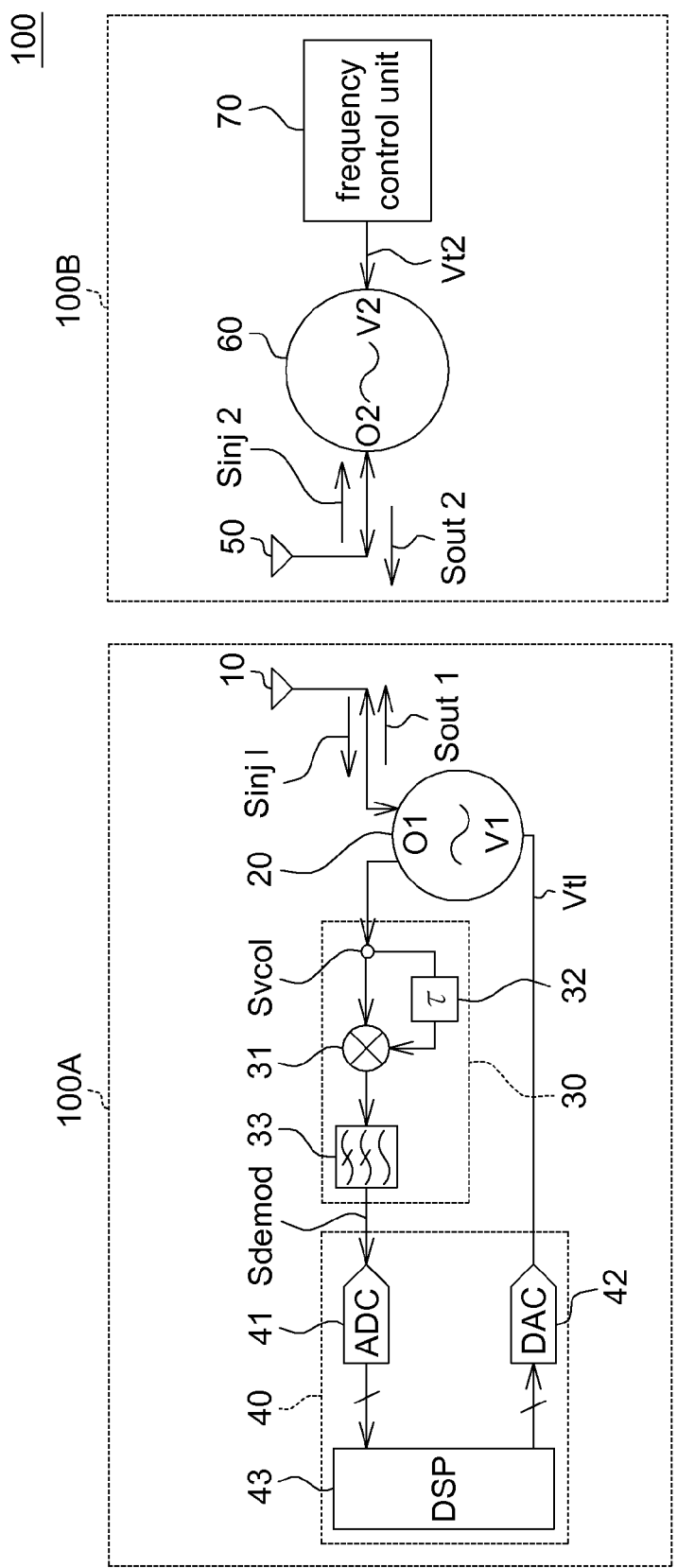
FIG. 2 shows a module diagram of a non-contact vital sign sensing system according to the embodiment of the disclosure.

FIG. 2 shows a module diagram of the non-contact vital sign sensing system 100 according to an embodiment of the disclosure is shown. In the present embodiment of the disclosure, the frequency demodulation unit 30 such as includes a mixer 31, a delay unit 32 and a filter 33. The signal processing unit 40 such as includes an analog-to-digital converter (ADC) 41, a digital-to-analog converter (DAC) 42 and a digital signal processor (DSP) 43. In alternate embodiments of the disclosure, the frequency demodulation unit 30 and the signal processing unit 40 may have alternate configurations.

The VCO 20 has a voltage input port V1 and a differential signal output port O1. The antenna 10 is electrically connected to the differential signal output port O1 of the VCO 20 for transmitting a signal Sout1 towards the heart at the front side of the body. In the present embodiment of the disclosure, the VCO 20 outputs differential output signals Sout1 and Svco1, wherein the differential output signal Sout1 is inputted to the antenna 10 and the differential output signal Svco1 is inputted to the frequency demodulation unit 30.

In the present embodiment of the disclosure, the VCO 20 generates differential output signals Sout1 and Svco1 in many implementations. In one implementation, the VCO 20 generates a single differential output signal and the single differential output signal is divided into the differential output signals Sout1 and Svco1 by a power divider. Under such implementation, the differential output signals Sout1 and Svco1 are identical to each other. In an alternate implementation, the VCO 20 directly outputs two differential output signals Sout1 and Svco1, and the phases of the two differential output signals Sout1 and Svco1 are not necessary the same.

The VCO 60 has a voltage input port V2 and a differential signal output port O2. The antenna 50 is electrically connected to the signal output port O2 of the VCO 60 for transmitting a signal Sout2 towards the heart at the back side of the body.

In the present embodiment of the disclosure, a signal Sinj1 includes a reflected signal from the object (such as the signal reflected from the heart at the front side of a body) and the signal Sout2 transmitted to the vital sign sensing module 100A by the body movement interference cancellation module 100B/100B'. The signal Sinj1 is received by the antenna 10 of the vital sign sensing module 100A and electrically connected to the differential signal output port O1 of the VCO 20. The signal Sinj2 includes a reflected signal from the object (such as the signal reflected from the heart at the back side of a body) and the signal Sout1 transmitted to the body movement interference cancellation module 100B/100B' by the vital sign sensing module 100A. The signal Sinj2 is received by the antenna 50 of the body movement interference cancellation module 100B/100B' and is electrically connected to the differential signal output port O2 of the VCO 60. The vital sign sensing module 100A generate a SIL mechanism and an MIL mechanism for example at the same time and so is the body movement interference cancellation module 100B/100B'. In the present embodiment of the disclosure, the vital sign (such as breathing and heartbeat) is isotropic to the vital sign sensing module 100A and the body movement interference cancellation module 100B/100B'; and the body movement signal is anisotropic to the vital sign sensing module 100A and the body movement interference cancellation module 100B/100B'.

Through the SIL mechanism, the vital sign sensing module 100A and the body movement interference cancellation module 100B/100B' obtain the same physiological information, and the anisotropic body movement information is cancelled at the radio frequency front end module.

In the present embodiment of the disclosure, the frequency demodulation unit 30 of the vital sign sensing module 100A is electrically connected to another end of the differential signal output port O1 of the VCO 20 for observing the frequency variation of the output signal Sout1 of the VCO 20.

The mixer 31 is electrically connected to another end of the differential signal output port O1 of the VCO 20 for mixing the differential output signal Svco1 and the output signal of the delay unit 32. Two ends of the delay unit 32 are electrically connected to the mixer 31 and the another end of the differential signal output port O1 of the VCO 20, for delaying and inputting the differential output signal Svco1 to the mixer 31. The filter 33, such as a low-pass filter, is electrically connected to an output end of the mixer 31 for filtering the mixer 31 (such as filtering off high-frequency noises).

The signal processing unit 40 is electrically connected to an output end of the low-pass filter 33 and the voltage input port V1 of the VCO 20. The signal processing unit 40 outputs an analog control voltage Vt1 and the analog control voltage Vt1 adjusts the output frequency of the VCO 20. The frequency control unit 70 of the body movement interference cancellation module 100B' is electrically connected to the voltage input port V2 of the VCO 60. The frequency control unit 70 outputs an analog control voltage Vt2 and the analog control voltage Vt2 adjusts the output frequency of the VCO 60. The vital sign sensing module 100A and the body movement interference cancellation module 100B/100B' have the same operating frequency for being operated under an MIL mode.

The ADC 41 is electrically connected to an output end of the frequency demodulation unit 30 for performing analog-to-digital conversion on the output signal of the filter 33. The DAC 42 is electrically connected to the voltage input port V1 of the VCO 20. The digital signal processor 43 is electrically connected to the ADC 41 and DAC 42. The digital signal processor 43 processes the digital output signal of the ADC 41 to produce results (such as a vital sign of the body). In addition, the digital signal processor 43 generates a digital control signal to the DAC 42. The DAC 42 performs digital-to-analog conversion on the digital control signal generated by the digital signal processor 43 to generate the analog control voltage Vt1 for controlling the oscillation frequency of the VCO 20.

The frequency demodulation unit 30 receives the differential signal output signal Svco1 of the VCO 20 to generate a narrow-band analog signal Sdemod. The ADC 41 samples the narrow-band analog signal Sdemod, and the digital signal processor 43 identifies/determines the sampling result to obtain wave patterns and frequency patterns of breathing and heartbeat in time domain.

Figure 3:
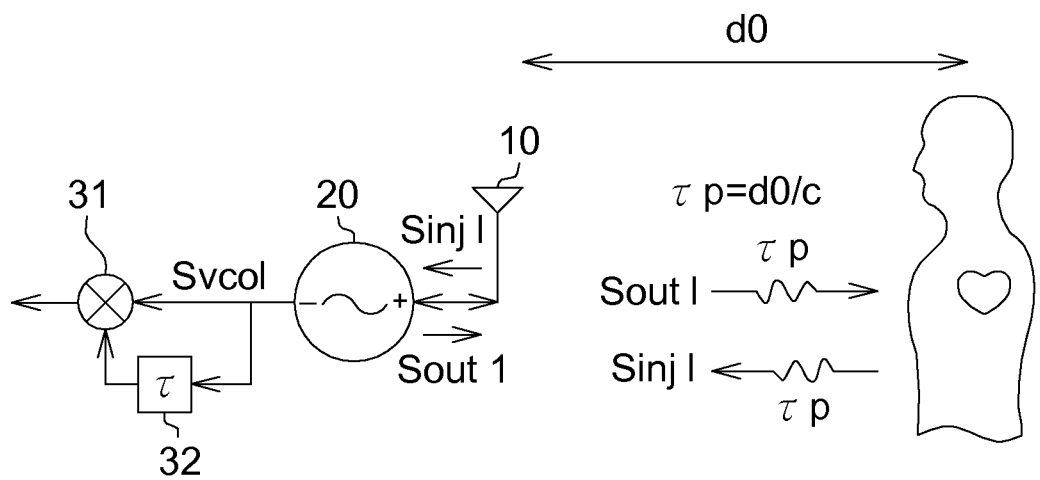
FIG. 3 shows a schematic diagram of a Doppler radar sensor using SIL according to the embodiment of the disclosure.

FIG. 3 shows a schematic diagram of a Doppler radar sensor using SIL mechanism according to an embodiment of the disclosure. The position of the antenna 10 is different from the position of an object by d0, and the signal Sout1 transmitted towards the VCO 20 reaches the surface of the chest cavity after a delay πp, wherein πp=d0/c, and c denotes the speed of light. Heartbeat and breathing make the chest cavity heave and generate Doppler Effect, which modulates the phase of the radio frequency signal Sout1. The signal reflected from the body is received by the antenna 10 after πp and injected to the VCO 20 such that the VCO 20 enters an SIL mode. Another output signal Svco1 of the VCO 20 is transmitted and demodulated into a base band signal by the frequency demodulator 30 for the rear-end signal processing unit 40 to determine the physiological information.

Figure 4:
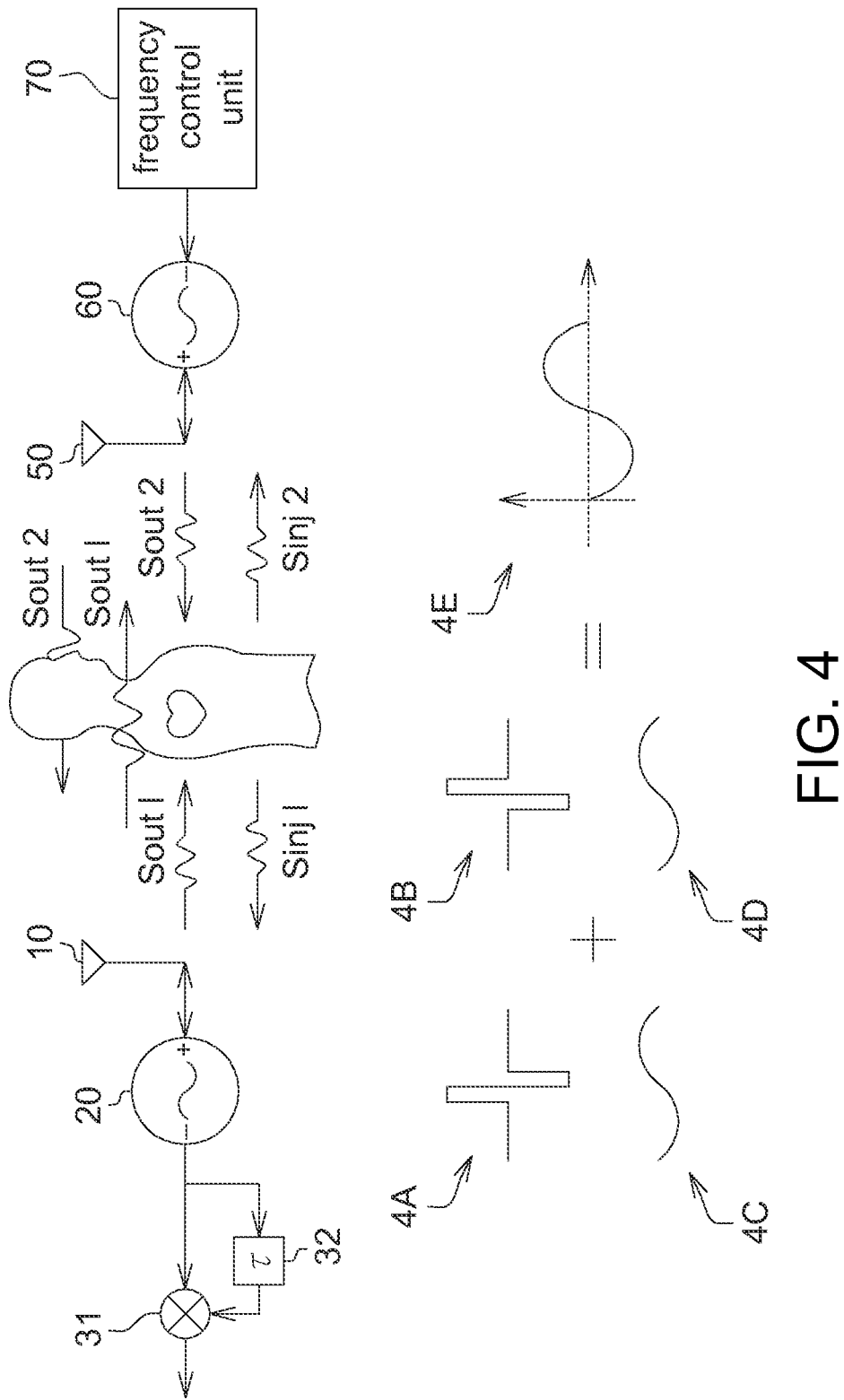
FIG. 4 shows a schematic diagram of canceling body movement interference at a radio frequency end by MIL according to the embodiment of the disclosure.

FIG. 4 shows a schematic diagram of using MIL to cancel body movement interference at a radio frequency end according to one embodiment of the disclosure. In the present embodiment of the disclosure, for canceling body movement interference, at least two sensing modules 100A and 100B are used. As disclosed above, the body movement is in one direction, but the expansion/contraction of the lung or the heart is a plurality of directions or omni directional. The sensing modules 100A and 100B sense vital sign and body movement according to the SIL mechanism, and achieve synchronization through MIL for canceling body movement information but obtaining the physiological information.

In FIG. 4, designations 4A and 4B denote the body movement signals sensed by the vital sign sensing module 100A and the body movement interference cancellation module 100B respectively; designations 4C and 4D denote the vital sign sensed by the vital sign sensing module 100A and the body movement interference cancellation module 100B respectively; and designation 4E denotes the vital sign after the body movement signal is cancelled. That is, the vital sign still may be sensed even when the body is moving.

Figure 5A:
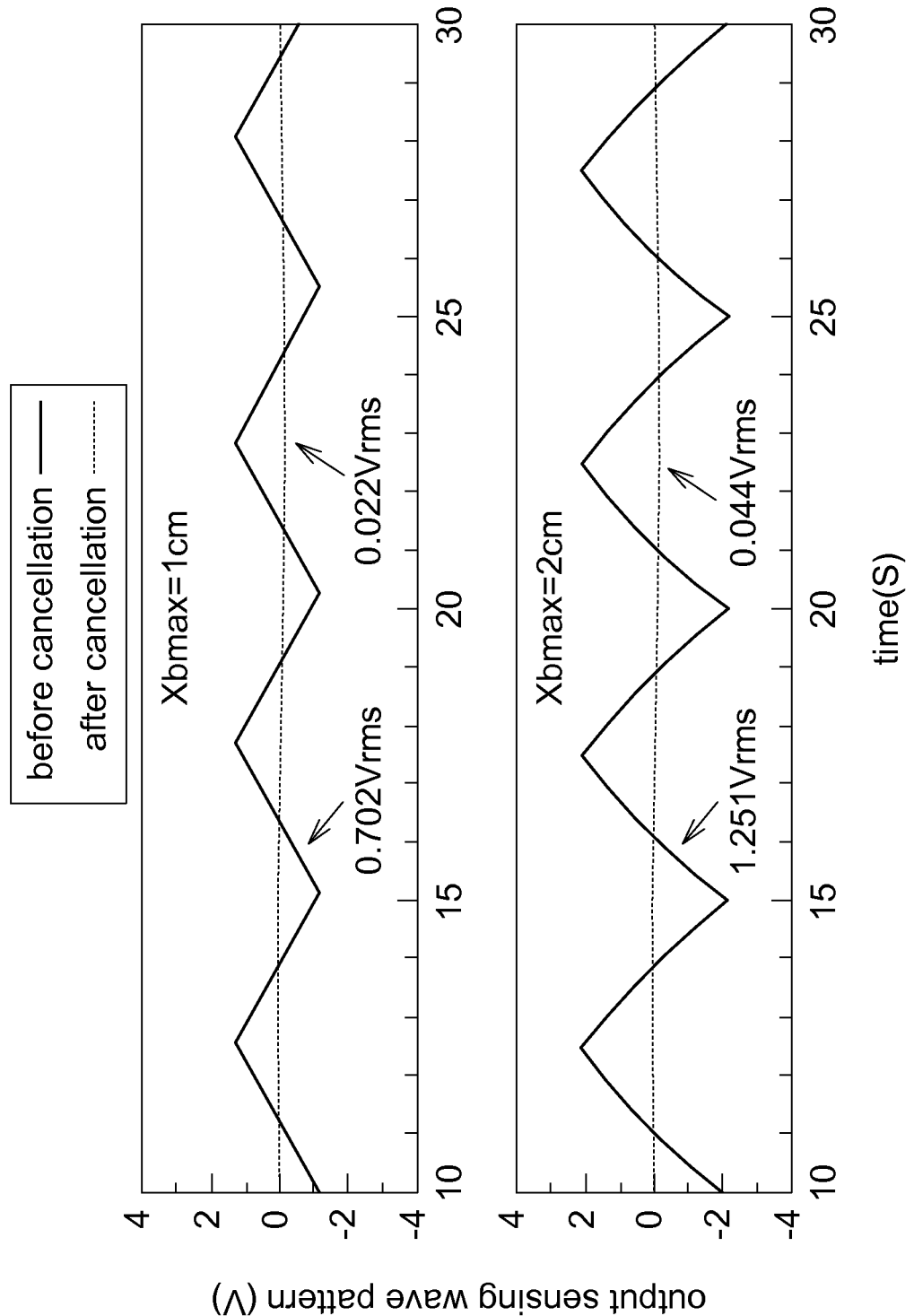
FIGS. 5A~5B are experimental sensing results showing the cancellation effect for regular movement according to one embodiment of the disclosure.
Figure 5B:
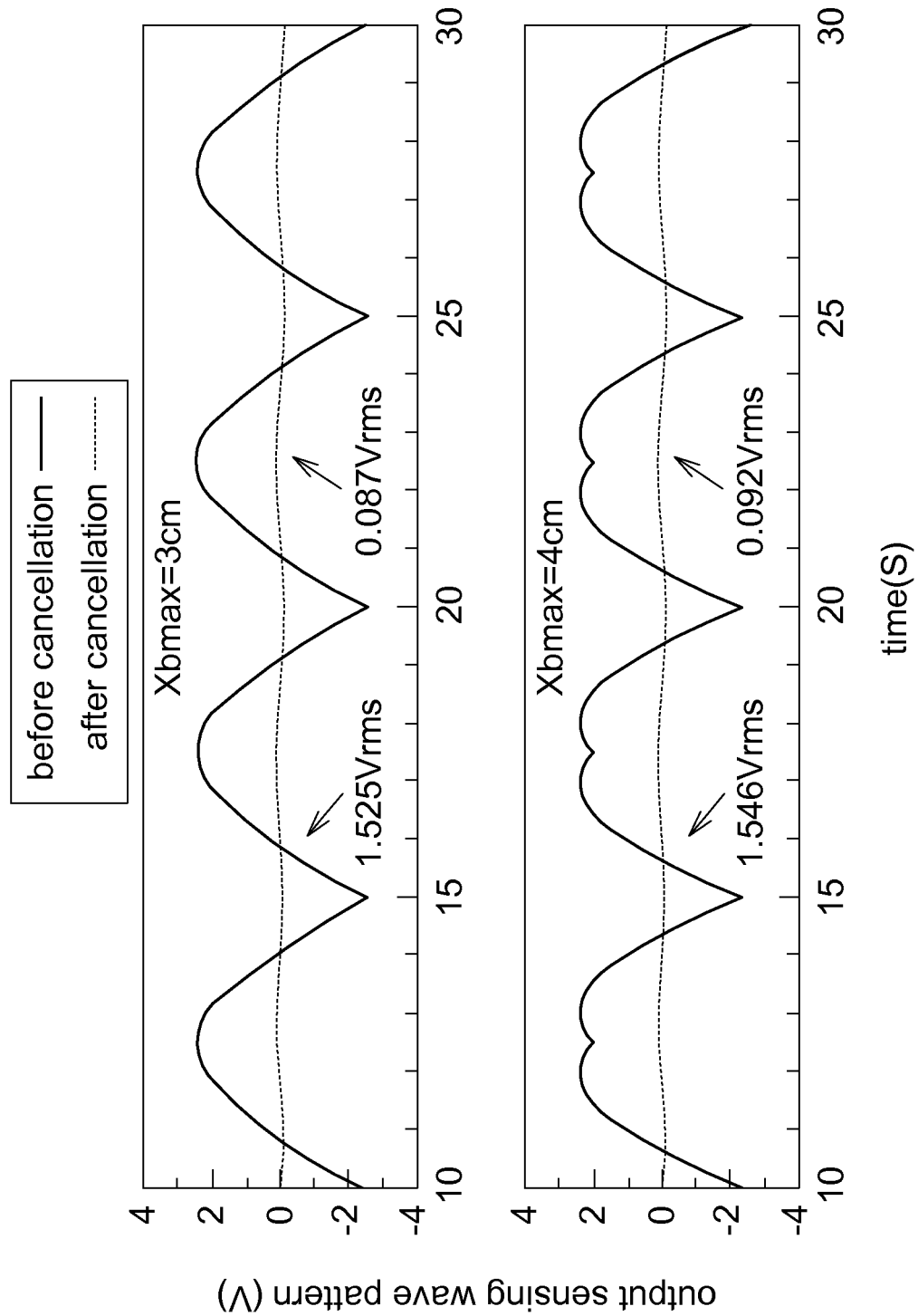

Referring to FIGS. 5A~5B, experimental sensing results showing the cancellation effect for regular movement according to one embodiment of the disclosure are shown. For example, let a metal plate be placed in the sensing system to simulate the body movement. The metal plate moves periodically for 1 cm, 2 cm, 3 cm and 4 cm. In FIG. 5A and FIG. 5B, the solid lines are sensing results by the vital sign sensing module 100A, and the dotted lines are sensing results by the vital sign sensing module 100A and the body movement interference cancellation module 100B. The comparison of root mean square between the two lines shows that cancellation effect is more than 90%. The comparison shows that the present embodiment of the disclosure has the effect of canceling body movement.

Figure 6A:
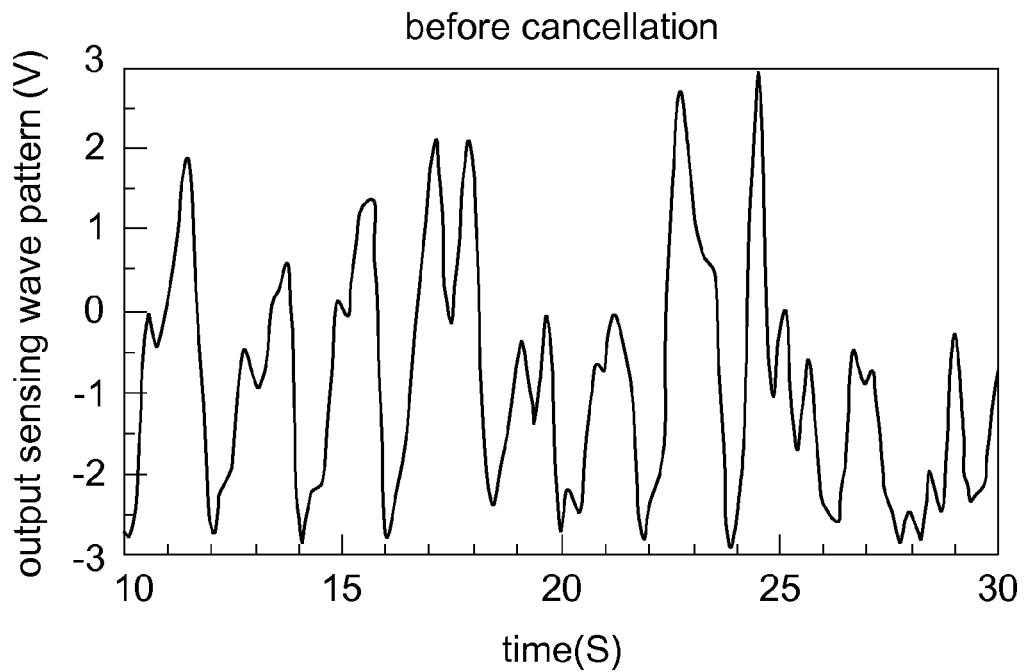
FIGS. 6A~6D are experimental sensing results showing the cancellation effect for random (irregular) movement according to one embodiment of the disclosure.
Figure 6B:
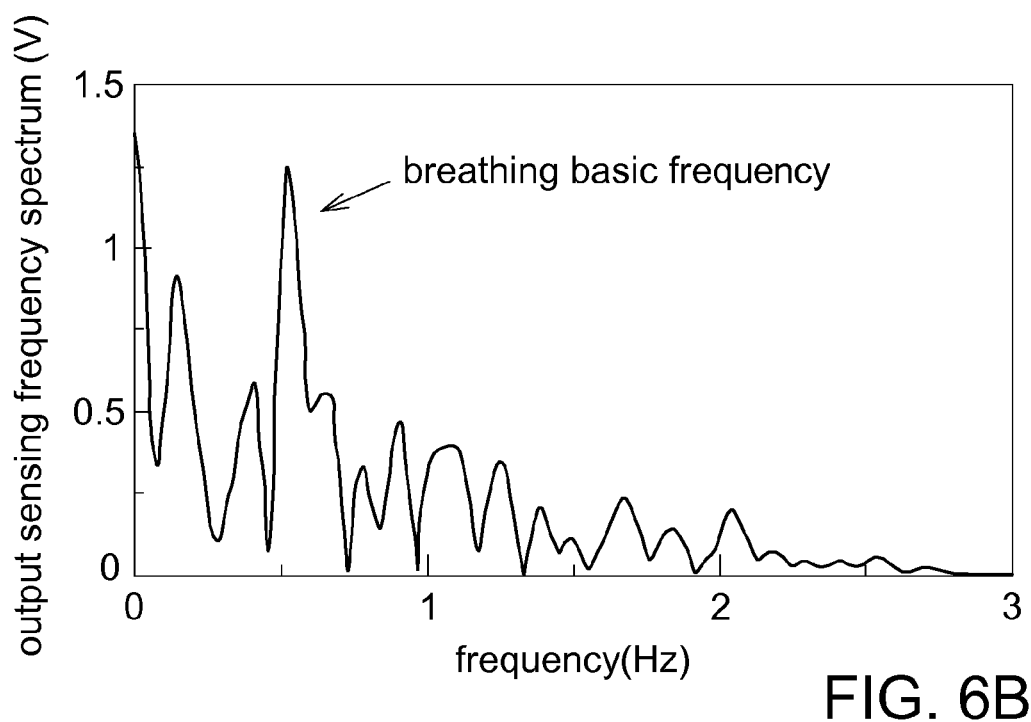

Referring to FIGS. 6A~6D, experimental sensing results showing the cancellation effect for random (irregular) movement according to one embodiment of the disclosure are shown. FIGS. 6A and 6B (before cancellation) show the sensing results obtained by only the vital sign sensing module 100A when the object is running on a treadmill. FIGS. 6A and 6B respectively show the time domain wave patterns and the time-domain frequency patterns of the sensing results before cancellation. Due to the random movement of the body, the wave patterns show dramatic and irregular ups and downs. After Fourier transform, as indicated in the frequency spectrum of FIG. 6B, only 0.5 Hz breathing basic frequency is recognized, but the heartbeat basic frequency and the random body movement signal are not recognized.

Figure 6C:
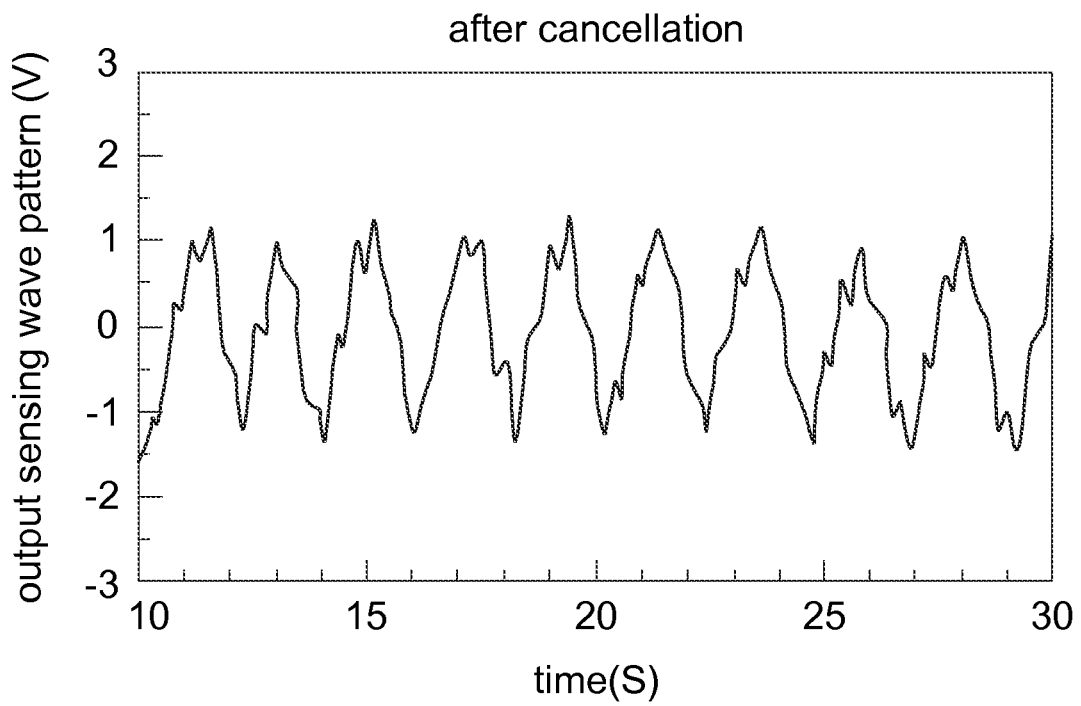
Figure 6D:
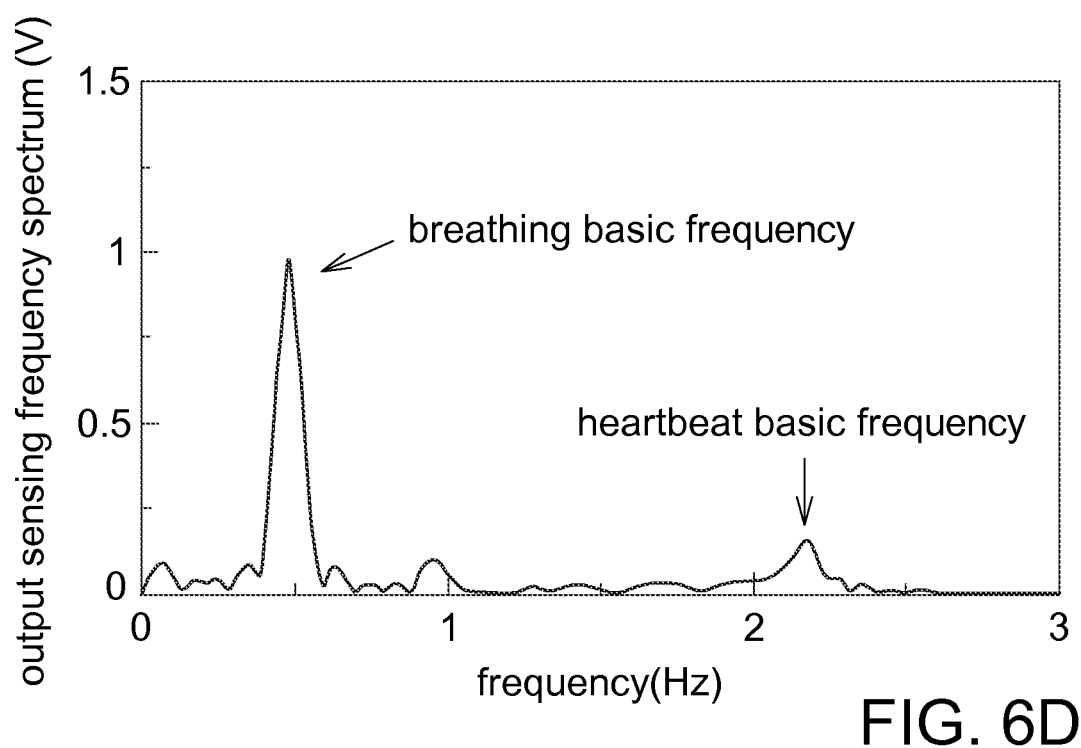

FIGS. 6C and 6D (after cancellation) show the sensing results obtained by the vital sign sensing module 100A and the body movement interference cancellation module 100B when the object is running on a treadmill. FIGS. 6C and 6D respectively show the time domain wave patterns and the time domain frequency patterns of the sensing results after cancellation. The wave patterns of FIG. 6C and FIG. 6D are regular and include physiological information (such as breathing and heartbeat). As indicated in the frequency spectrum of FIG. 6D, the breathing basic frequency and the heartbeat basic frequency are recognized in the present embodiment of the disclosure and are about 0.5 Hz and 2.16 Hz respectively, that is, 30 breathings per minute and 130 heartbeats per minute. These are conformed to the sensing results obtained by other medical care apparatuses.

In the present embodiment of the disclosure, the signal transmission end and the signal reception end are the same end point (the differential signal output end of the VCO), and no separation module is between the said end point and the antenna. In addition, since the present embodiment of the disclosure adopts MIL, the two sensing modules 100A and 100B are coupled through a radio frequency signal, such that the sensing modules 100A and 100B are synchronized.

The non-contact vital sign sensing system of the present embodiment of the disclosure for canceling body movement interference is based on the SIL mechanism and the MIL mechanism. In comparison to the conventional vital sign sensing module which has the Doppler radar configuration and uses the base band signal processing technology, the present embodiment of the disclosure might increase sensing sensitivity by the SIL mechanism and might reduce module elements, system complexity and power consumption by canceling the body movement signal at the front end of radio frequency module by the MIL mechanism.

In the present embodiment of the disclosure, the sensing modules are operated under the same frequency and the polarization direction; and the sensing modules are synchronized through the MIL mechanism. Thus, the random body movement interference is cancelled at the front end of radio frequency module. Since the information obtained by the two sensing modules is consistent, using one base-band signal output, and system configuration is thus simplified in principle.

In principle, since the body movement interference is cancelled during sensing, the present embodiment of the disclosure provides more reliable and accurate sensing results of vital signs. The application of the present embodiment of the disclosure includes but not limited to the areas such as the long period monitoring of cardiopulmonary patients' breathing and heartbeat, the prevention of sudden infant death, and the vital sign monitoring of sports and fitness equipment. Therefore, the application of the present embodiment of the disclosure is not restricted by the sensing place, making the medical resources more effectively utilized. The present embodiment of the disclosure may be used in the entertainment industry such as the somatosensory entertainment which generates corresponding movement in response to the body movement or may be used in other suitable areas.

Figure 7A:
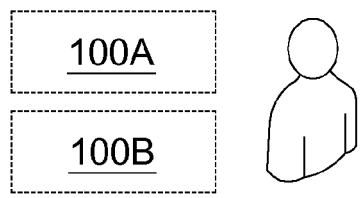
FIGS. 7A~7C are system block diagrams of a non-contact vital sign sensing system according to alternate embodiments of the disclosure.
Figure 7B:
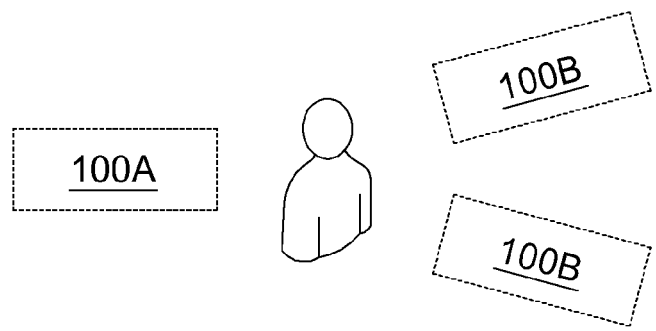
Figure 7C:
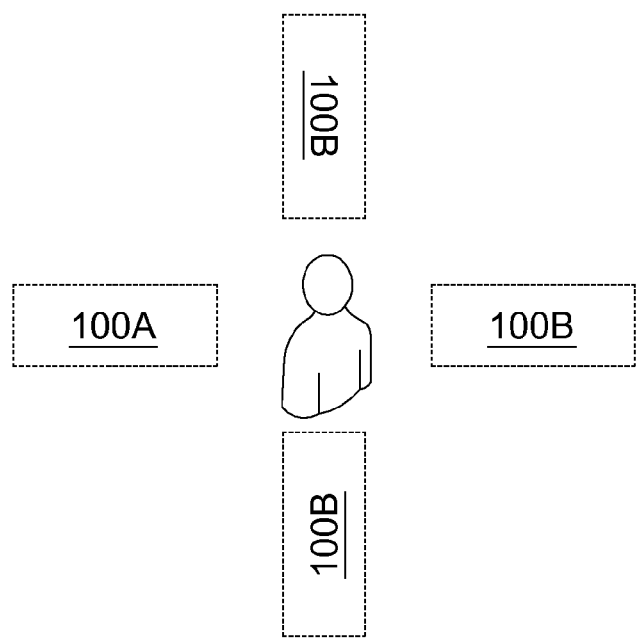

Referring to FIGS. 7A~7C, system block diagrams of non-contact vital sign sensing systems according to alternate embodiments of the disclosure are shown. FIG. 7A shows that the vital sign sensing module 100A and the body movement interference cancellation module 100B are placed at the same side of an object and are still able to cancel body movement interference. In FIG. 1, the vital sign sensing module 100A and the body movement interference cancellation module 100B are respectively placed at the front side and the rear side of an object. As indicated in FIG. 7A, the vital sign sensing module 100A faces towards the chest cavity and the body movement interference cancellation module 100B faces towards the abdominal cavity. By adjusting the positions and operating frequencies of the two sensing modules 100A and 100B, the two sensing modules 100A and 100B sense anisotropic body movement signals, and sensing module 100A senses vital sign information. Due to the MIL mechanism, the two sensing modules 100A and 100B at the same side of the object still cancel body movement interference.

In alternate embodiments of the disclosure, multi-dimensional body movement interference is cancelled as indicated in FIG. 7B and FIG. 7C. The module configurations illustrated in FIG. 7B and FIG. 7C both cancel two-dimensional body movement interference. The module configuration illustrated in FIG. 7B and FIG. 7C employ several sensing modules having the same operating frequency but process one set of base band signal. Since one vital sign sensing module 100A is enough, system cost and module complexity could be effectively reduced.

In alternate embodiments of the disclosure, the frequency demodulation unit has other ways of implementation in addition to the implementation illustrated in FIG. 2. FIGS. 8A~8D show alternate implementations of a frequency demodulation unit according to other embodiments of the disclosure.

Figure 8A:
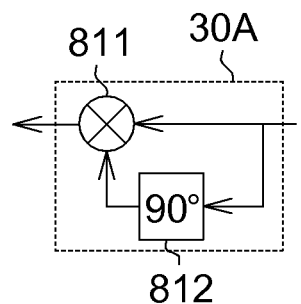
FIGS. 8A~8D are alternate implementations of a frequency demodulation unit according to other embodiments of the disclosure.

As indicated in FIG. 8A, the frequency demodulation unit 30A is an orthogonal demodulator which includes a mixer 811 and a phase shift unit 812. The phase shift unit 812 adjusts the phase of the input frequency modulation signal, such that the phase difference between the input signal and the output signal is 90 degrees. The mixer 811 mixes the input frequency modulation signal with the output signal of the phase shift unit 812 to obtain a demodulation signal.

Figure 8B:
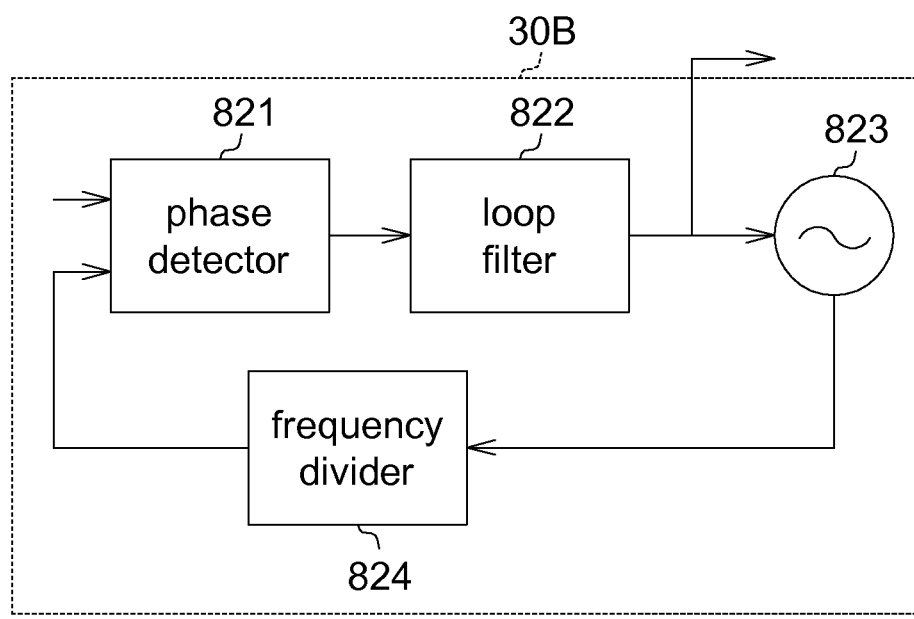

As indicated in FIG. 8B, the frequency demodulation unit 30B is a PLL demodulator and includes a phase detector 821, a loop filter 822, a VCO 823 and a frequency divider 824. The configuration of FIG. 8B is similar to a phase locked loop (PLL), and is thus called a PLL demodulator. The phase detector 821 compares the phase of the input frequency modulation signal with that of the signal generated by the VCO 823 and/or the frequency divider 824. The loop filter 822 performs loop filtering on the phase comparison result obtained by the phase detector 821 to generate a frequency control voltage. The frequency control voltage locks the frequency of the VCO 823 such that the input frequency modulation signal and the VCO output signal are synchronized. The frequency adjustment voltage is the frequency modulation information of the frequency modulation signal.

Figure 8C:
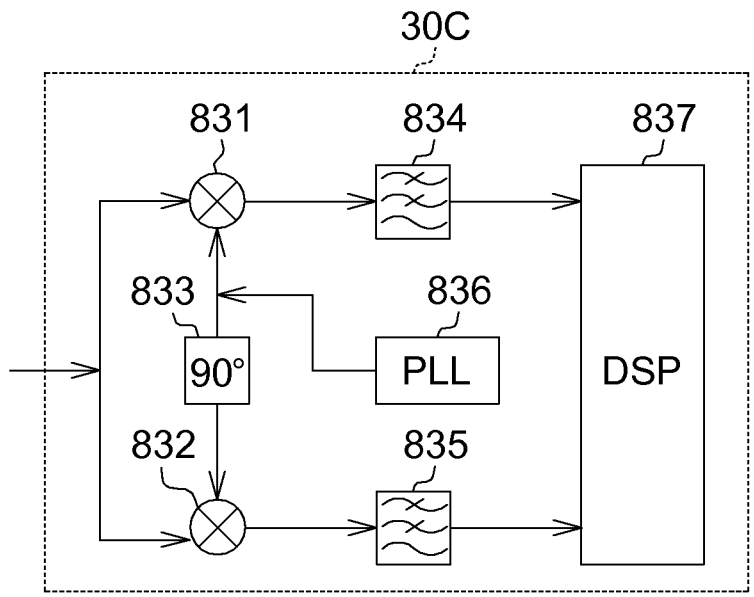

As indicated in FIG. 8C, the frequency demodulation unit 30C is a synchronic demodulator-IQ demodulator and includes mixers 831 and 832, a phase shift unit 833, low-pass filters 834 and 835, a PLL 836 and a digital signal processor (DSP) 837. The input frequency modulation signal is inputted to the mixers 831 and 832. Switch signals of the mixers 831 and 832 are provided by the PLL 836, wherein the phase difference between the switch signals applied to the mixers 831 and 832 is 90 degrees. The output signals of the mixers 831 and 832 are filtered off by the low-pass filters 834 and 835 to filter cross-modulation signals and frequency modulation information is output by the DSP 837.

Figure 8D:
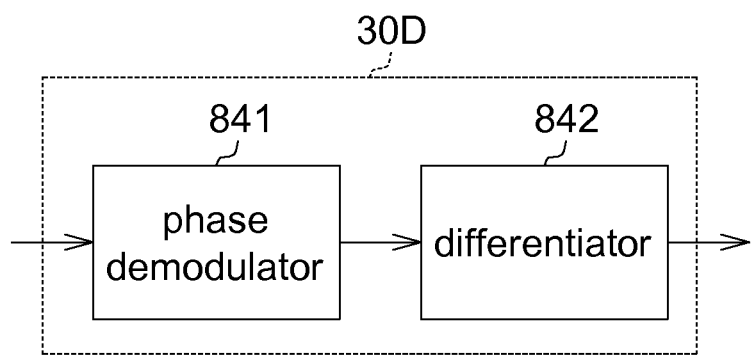

As indicated in FIG. 8D, the frequency demodulation unit 30D includes a phase demodulator 841 and a differentiator 842. The input frequency modulation signal is inputted to the phase demodulator 841 so as to obtain the phase variation. The differentiator 842 performs differentiation to obtain frequency modulation information.

Figure 9:
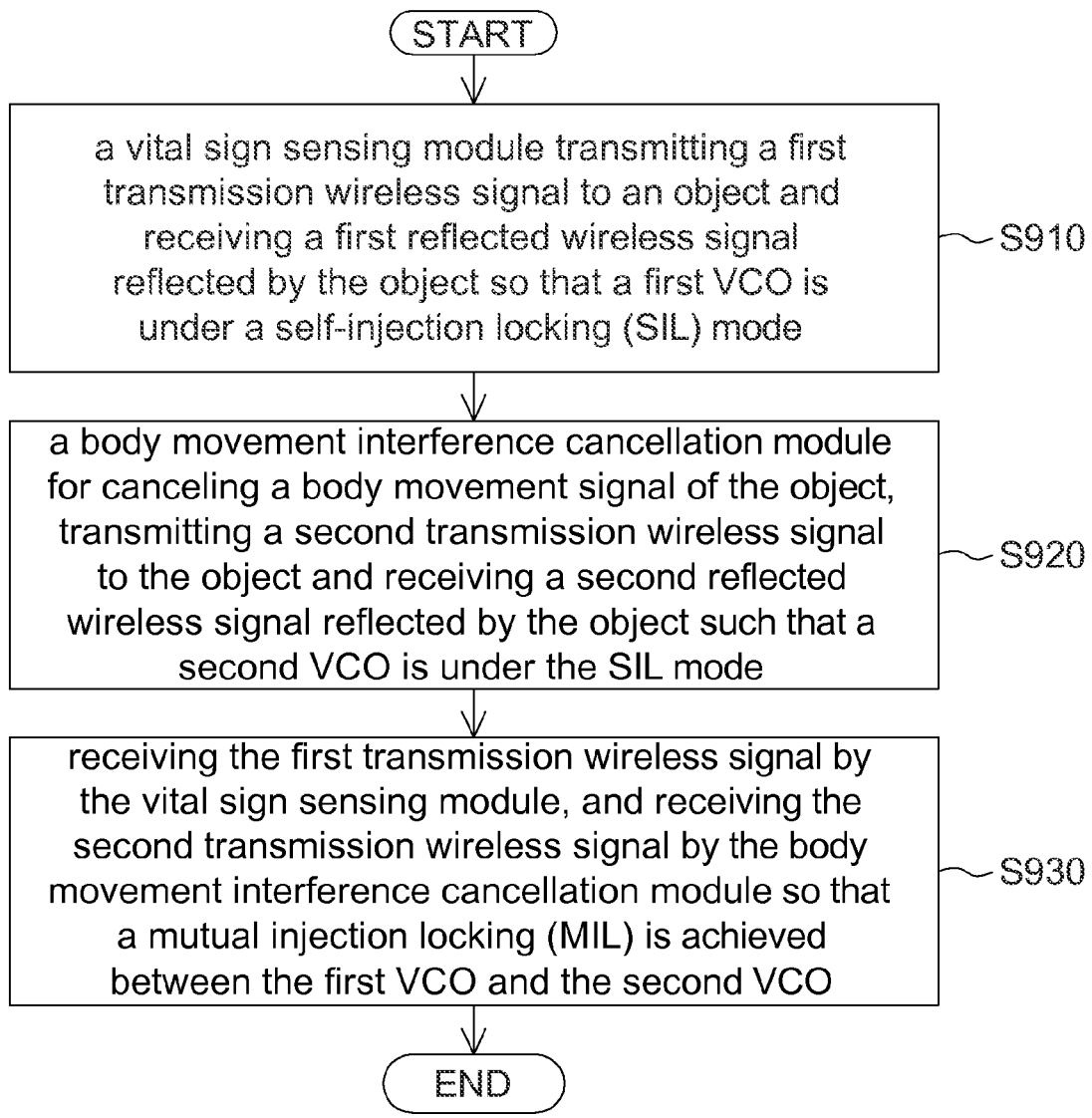
FIG. 9 is a flow chart for non-contact vital signal sensing method according to other embodiments of the disclosure.

FIG. 9 is a flow chart for non-contact vital signal sensing method according to other embodiments of the disclosure. The non-contact vital sign sensing method includes: S910, a vital sign sensing module transmitting a first transmission wireless signal to an object and receiving a first reflected wireless signal reflected by the object so that a first VCO is under a self-injection locking (SIL) mode; S920, a body movement interference cancellation module for canceling a body movement signal of the object, transmitting a second transmission wireless signal to the object and receiving a second reflected wireless signal reflected by the object such that a second VCO is under the SIL mode; and S930, receiving the first transmission wireless signal by the vital sign sensing module, and receiving the second transmission wireless signal by the body movement interference cancellation module so that a mutual injection locking (MIL) is achieved between the first VCO and the second VCO. Details of steps S910-S930 are as the above description and thus they are omitted here.

Further, in the above embodiments, the vital sign sensing module and/or the body movement interference cancellation module may be implemented by hardware circuits. However, in other possible embodiments, a part of the vital sign sensing module and/or the body movement interference cancellation module may be implemented by software an/or firmware.

It will be appreciated by those skilled in the art that changes could be made to the disclosed embodiments described above without departing from the broad inventive concept thereof. It is understood, therefore, that the disclosed embodiments are not limited to the particular examples disclosed, but is intended to cover modifications within the spirit and scope of the disclosed embodiments as defined by the claims that follow.

What is claimed is:

1. A non-contact vital sign sensing system, comprising:
a vital sign sensing module for sensing a vital sign of an object, comprising:
a first antenna for transmitting a first transmission wireless signal to the object and receiving a first reflected wireless signal reflected from the object;
a first voltage control oscillator (VCO) directly connected to the first antenna for outputting the first transmission wireless signal to the first antenna and receiving the first reflected wireless signal via the first antenna, and accordingly the vital sign sensing module is under a self-injection locking (SIL) mode;
a frequency demodulation unit coupled to the first VCO for demodulating a frequency variation of the first VCO; and
a signal processing unit coupled to the frequency demodulation unit and the first VCO for obtaining the vital sign of the object based on the frequency variation of the first VCO and for determining a first oscillation frequency of the first VCO; and at least one body movement interference cancellation module wirelessly coupled to the vital sign sensing module, for canceling a body movement signal of the object, wherein each body movement interference cancellation module comprises:

a second antenna for transmitting a second transmission wireless signal to the object and receiving a second reflected wireless signal reflected by the object; and a second VCO directly connected to the second antenna for outputting the second transmission wireless signal to the second antenna and for receiving the second reflected wireless signal via the second antenna, and accordingly the at least one body movement interference cancellation module is under the SIL mode;

wherein, the first antenna transmits the first transmission wireless signal to the second antenna of the at least one body movement interference cancellation module, and the first transmission wireless signal is received by the second VCO via the second antenna;

the second antenna transmits the second transmission wireless signal to the first antenna of the vital sign sensing module, and the second transmission wireless signal is received by the first VCO via the first antenna; and accordingly a mutual injection locking (MIL) mode is achieved between the vital sign sensing module and the at least one body movement interference cancellation module.

2. The non-contact vital sign sensing system according to claim 1, wherein, the first transmission wireless signal and the first reflected wireless signal have different frequencies; and the second transmission wireless signal and the second reflected wireless signal have different frequencies.

3. The non-contact vital sign sensing system according to claim 1, wherein, the body movement interference cancellation module further comprises a frequency control unit coupled to the second VCO for determining a second oscillation frequency of the second VCO; and the first oscillation frequency of the first VCO is the same with the second oscillation frequency of the second VCO.

4. The non-contact vital sign sensing system according to claim 1, wherein, the vital sign of the object is isotropic to the vital sign sensing module and the at least one body movement interference cancellation module.

5. The non-contact vital sign sensing system according to claim 4, wherein, the body movement signal of the object is anisotropic to the vital sign sensing module and the at least one body movement interference cancellation module.

6. The non-contact vital sign sensing system according to claim 5, wherein, during sensing, the vital sign sensing module and the at least one body movement interference cancellation module are located at opposite sides of the object.

7. The non-contact vital sign sensing system according to claim 5, wherein, during sensing, the vital sign sensing module and the at least one body movement interference cancellation module are located at the same side of the object.

8. The non-contact vital sign sensing system according to claim 1, further comprising a plurality of body movement interference cancellation modules for transmitting a plurality of second transmission wireless signals to the object from a plurality of directions for canceling a multi-dimensional body movement signal of the object.

9. A non-contact vital sign sensing method, comprising:

a vital sign sensing module transmitting a first transmission wireless signal to an object and receiving a first reflected wireless signal reflected by the object and accordingly a first VCO is under a self-injection locking (SIL) mode;

a body movement interference cancellation module for canceling a body movement signal of the object, transmitting a second transmission wireless signal to the object and receiving a second reflected wireless signal reflected by the object and accordingly a second VCO is under the SIL mode; and receiving the second transmission wireless signal by the vital sign sensing module, and receiving the first transmission wireless signal by the body movement interference cancellation module and accordingly a mutual injection locking (MIL) is achieved between the first VCO and the second VCO.

10. The non-contact vital sign sensing method according to claim 9, further comprising:

transmitting the first transmission wireless signal to the object via a first antenna;

outputting the first transmission wireless signal to the first antenna by the first VCO, wherein the first VCO receives the first reflected wireless signal via the first antenna, and accordingly the first VCO is under the self-injection locking (SIL) mode;

demodulating a frequency variation of the first VCO;

obtaining a vital sign of the object from the frequency variation of the first VCO and determining a first oscillation frequency of the first VCO;

transmitting the second transmission wireless signal to the object via a second antenna; and outputting the second transmission wireless signal to the second antenna by the second VCO, wherein the second VCO receives the second reflected wireless signal via the second antenna, and accordingly the second VCO is under the SIL mode;

wherein, the first antenna transmits the first transmission wireless signal to the second antenna, and the first transmission wireless signal is received by the second VCO via the second antenna;

the second antenna transmits the second transmission wireless signal to the first antenna, and the second transmission wireless signal is received by the first VCO via the first antenna;

the first transmission wireless signal and the first reflected wireless signal have different frequencies; and the second transmission wireless signal and the second reflected wireless signal have different frequencies.

11. The non-contact vital sign sensing method according to claim 10, further comprising:

determining a second oscillation frequency of the second VCO;

wherein, the first oscillation frequency of the first VCO is the same with the second oscillation frequency of the second VCO.

12. The non-contact vital sign sensing method according to claim 10, wherein, the vital sign of the object is an isotropic signal.

13. The non-contact vital sign sensing method according to claim 12, wherein, the body movement signal of the object is an anisotropic signal.

14. The non-contact vital sign sensing method according to claim 13, wherein, during sensing, the first transmission wireless signal and the second transmission wireless signal are transmitted to opposite sides of the object.

15. The non-contact vital sign sensing method according to claim 13, wherein, during sensing, the first transmission wireless signal and the second transmission wireless signal are transmitted to the same side of the object.

16. The non-contact vital sign sensing method according to claim 9, further comprising:
   transmitting a plurality of second transmission wireless signals to the object from a plurality of directions for canceling a multi-dimensional body movement signal of the object.

\* \* \* \* \*